United States Patent [19]

Kanbara et al.

[11] Patent Number: 5,628,962
[45] Date of Patent: May 13, 1997

[54] APPARATUS FOR OPENING AND CLOSING REAGENT CONTAINERS

[75] Inventors: Katsuhiro Kanbara; Hiroyasu Uchida, both of Hitachinaka, Japan

[73] Assignees: Hitachi, Ltd., Tokyo, Japan; Boehringer Mannheim GmbH, Mannheim, Germany

[21] Appl. No.: 530,602

[22] Filed: Sep. 20, 1995

[30] Foreign Application Priority Data

Sep. 21, 1994 [JP] Japan .................................. 6-226225

[51] Int. Cl.⁶ .................................................. G01N 35/10
[52] U.S. Cl. ...................... 422/63; 422/64; 422/104; 436/43; 436/47; 220/260; 220/263; 220/337; 222/549; 222/550; 222/556; 222/562; 215/235; 215/236; 215/239
[58] Field of Search ...................... 422/63, 64, 100, 422/102, 104; 436/43, 47, 49, 180; 215/235, 236, 239; 220/260, 263, 337; 222/545, 548, 549, 550, 556, 562, 563

[56] References Cited

U.S. PATENT DOCUMENTS

| | | |
|---|---|---|
| 4,455,280 | 6/1984 | Shinohara et al. |
| 5,271,897 | 12/1993 | Wurschum et al. .............. 422/63 |
| 5,289,930 | 3/1994 | Inouye ........................... 215/235 |
| 5,294,404 | 3/1994 | Grandone et al. .............. 422/64 |
| 5,358,691 | 10/1994 | Clark et al. ..................... 422/64 |

*Primary Examiner*—Long V. Le
*Attorney, Agent, or Firm*—Fay, Sharpe, Beall, Fagan, Minnich & McKee

[57] ABSTRACT

An analyzing apparatus has a movable container holding table on which a plurality of liquid containers are arranged. Each liquid container includes a container body accommodating a liquid such as a reagent, an opening portion, and a cap hinged to the container body. The analyzing apparatus further has a cap manipulator device including a hook for manipulating the cap so as to open and close the opening portion of the liquid container. The liquid in the liquid container whose opening portion is opened is aspirated through the opening portion and delivered to a liquid receiving container.

21 Claims, 8 Drawing Sheets

APPARATUS FOR OPENING AND CLOSING REAGENT CONTAINERS

BACKGROUND OF THE INVENTION

The present invention relates to an analyzing apparatus, and more particularly to an analyzing apparatus suitable for analyzing a liquid sample.

In recent years, biochemical analyzing apparatuses and immunity analyzing apparatuses have continuously operated for a long time because of centralization of examination and increase in analyzed items. During such a long operation, there occur evaporation of samples and reagents, and mixing of atmospheric dust into the samples and the reagents since it is natural for the samples and the reagents to be left in the atmosphere for a long time. In particular, change in concentration of a reagent cannot be neglected because it affects the analyzed result. It is, therefore, important to prevent the evaporation at least.

In the past, there have been generally few biochemical analyzing apparatuses and immunity analyzing apparatuses which take measures to actively prevent evaporation of the reagent in the apparatus. Therefore, when a reagent is used for a long time, scheduled calibrations with a comparatively short period are required since evaporation of the reagent is inevitable, and, accordingly, change in the concentration affects the accuracy of analysis.

A reagent supplying apparatus having a measure to prevent evaporation of reagent is disclosed in U.S. Pat. No. 4,455,280. The reagent supplying apparatus comprises a turntable supporting a plurality of reagent vessels, and caps attached to the turntable itself in one-to-one correspondence to the reagent are arranged on the turntable. In this conventional technology, the evaporation of liquid reagent is prevented by capping a reagent vessel with a spring-loaded cap.

In an apparatus in which a vessel and a cap are separately formed and the cap is attached to the apparatus in advance as in the reagent supplying apparatus of the U.S. Pat. No. 4,455,280, one-to-one correspondence between the vessel and the cap having the same content is always necessary because there is a possibility of carry-over due to attaching of the content in a vessel to a cap if the vessel is set at an arbitrary position to the cap arranged in a given position in the apparatus every time the vessel is set to the apparatus. This eliminates the freedom of setting vessel position.

Further, if the vessels and the caps are formed separately, an operator has to attach and detach the vessel caps every time the vessels are set to an apparatus or kept in a storage.

SUMMARY OF THE INVENTION

An object of the present invention is to provide an analyzing apparatus which includes a movable container holding table for holding a plurality of liquid containers each of which has a container body accommodating a liquid, an opening portion, and a cap attached to the container body so as to capable of opening and closing the opening portion.

Another object of the present invention is to provide an analyzing apparatus which is suitable for preventing an operator from attaching and detaching caps when liquid containers are set on a movable container holding table.

Also another object of the present invention is to provide an analyzing apparatus which is suitable for certainly opening the opening portion of the liquid container.

Yet another object of the present invention is to provide an analyzing apparatus in which there is no interference with the maintenance and inspection work of the movable container holding table.

Still another object of the present invention is to provide an analyzing apparatus which is capable of manipulating the caps so as to efficiently open and close the opening portions of the liquid containers.

According to the present invention, an analyzing apparatus is provided which comprises (1) a movable container holding table for holding a plurality of liquid containers, each of the liquid containers having a container body accommodating a liquid, an opening portion, and a cap attached to the container body so as to be capable of opening and closing the opening portion, (2) a cap manipulator for manipulating the cap so as to open the opening portion, and (3) a pipetter for aspirating the liquid in the container whose opening portion is opened therethrough and delivering the aspirated liquid to a liquid receiving container.

According to another aspect of the present invention, the analyzing apparatus further comprises means for moving the cap manipulator between a first and second positions spaced apart from each other, the cap manipulator manipulating the cap so as to open the opening portion at the first position.

According to a preferred embodiment of the present invention, the cap is hinged to the liquid container body to be rotatable about a first rotating axis.

According to another preferred embodiment of the present invention, each cap has a projecting portion, and the cap manipulator comprises a hook, the cap manipulator engaging the hook with the projecting portion and moving the hook so as to open the opening portion of the liquid container having the projecting portion with which the hook is engaged.

According to an additional preferred embodiment of the present invention, the hook has a second rotating axis positioned in the proximity of the first rotating axis so as to be rotated about the second rotating axis.

According to yet another preferred embodiment of the present invention, the cap manipulator rotates the hook around the second rotating axis in a first rotating direction so that the hook is directed to the cap, moves the hook in a horizontal direction so that the hook is located at a position at which the same is capable of being engaged with the projecting portion, and then rotates the hook around the second rotating axis in a second rotating direction, reverse to the first rotating direction with the hook being engaged with the projecting portion so as to open the opening portion.

According to a further preferred embodiment of the present invention, the cap manipulator comprises a contact portion integrated with the hook, the contact portion contacting the cap when the hook is rotated in the first rotating direction, and means for elastically urging the contact portion in the first rotating direction. Preferably, the contact portion urging means comprises a coil spring.

According to an additional aspect of the present invention, the cap manipulator rotates the hook in the first direction so as to bring the hook into contact with the cap to close the opening portion of the liquid container having the cap with which the hook is brought into contact.

According to yet another aspect of the present invention, the analyzing apparatus further comprises means for keeping the container body of the liquid container stationary when the opening portion thereof is opened.

According to a further aspect of the present invention, each cap has a projecting portion, and the cap manipulator comprises a plurality of hooks, the cap manipulator substantially simultaneously engaging the hooks with corresponding projecting portions and moving the hooks so as to substantially simultaneously open the opening portions of the liquid containers having the projecting portions with which the hooks are engaged.

According to a further additional aspect of the present invention, the cap manipulator rotates the hooks in the first direction so as to bring the hooks into contact with corresponding caps to substantially simultaneously close the opening portions of the liquid containers having the caps with which the hooks are brought into contact.

Other objects and features of the present invention will become apparent from the descriptions of preferred embodiments of the present invention taken in connection with the accompanying drawings.

DESCRIPTION OF THE PREFERRED EMBODIMENTS

Figure 1:
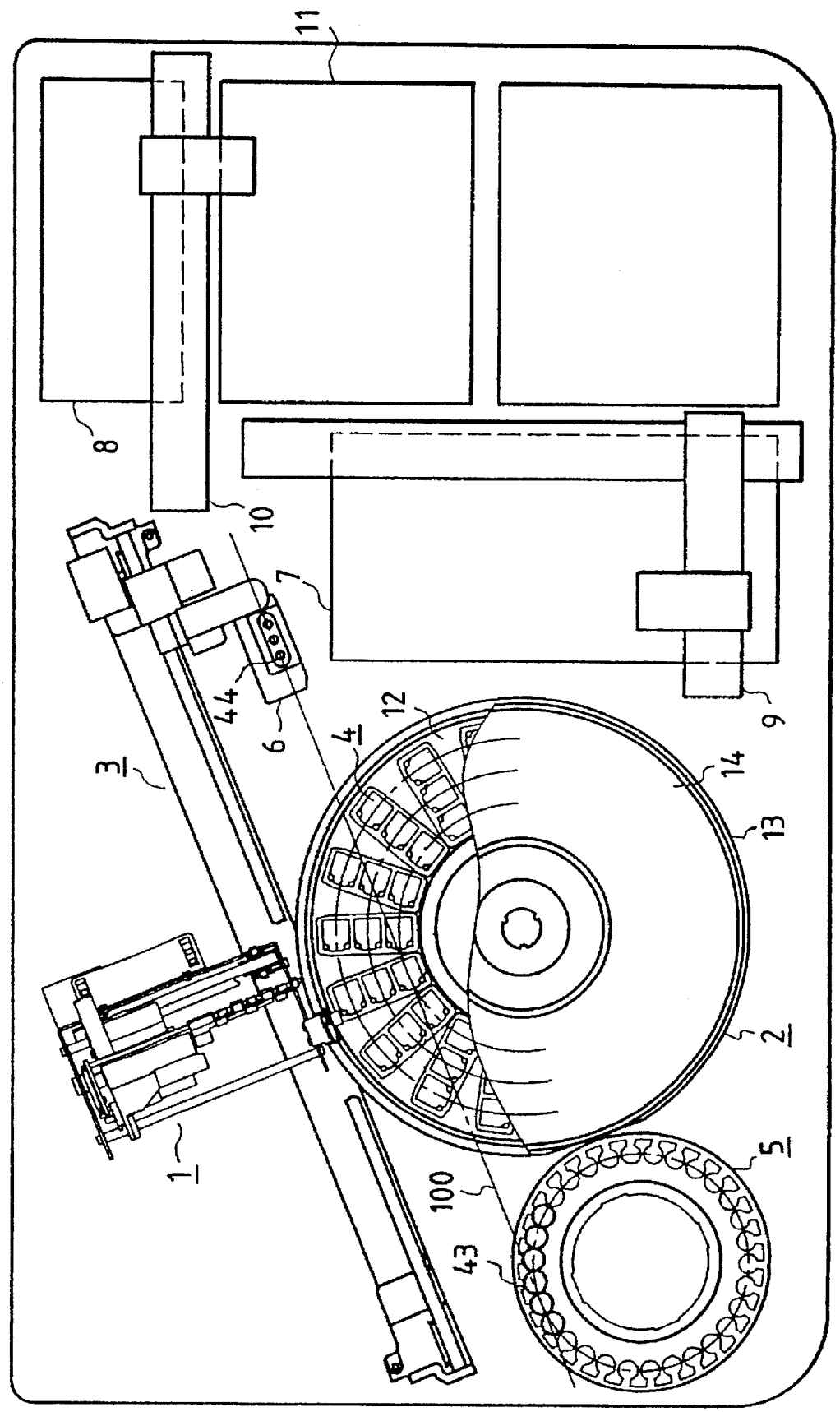
FIG. 1 is a schematic plan view of an embodiment of an analyzing apparatus in accordance with the present invention.

As shown in FIG. 1, a multiplicity of liquid bottles, vessels or containers 4 constitute container units for accommodating reagents arranged in a reagent container storing device 2, each container unit comprising three liquid containers prepared for each item to be measured or analyzed. Three liquid containers of each container unit are integrally aligned in a radial row and each of the container units is arranged on a movable container holding table for reagents, i.e., a rotatable reagent disk 12, as a transferring device. Arranged near the reagent container storing device 2 are a cap manipulator device 1, a sample container holding table 5, a pipetter 3 and so on. Operation of these components is controlled with a computer.

Figure 2:
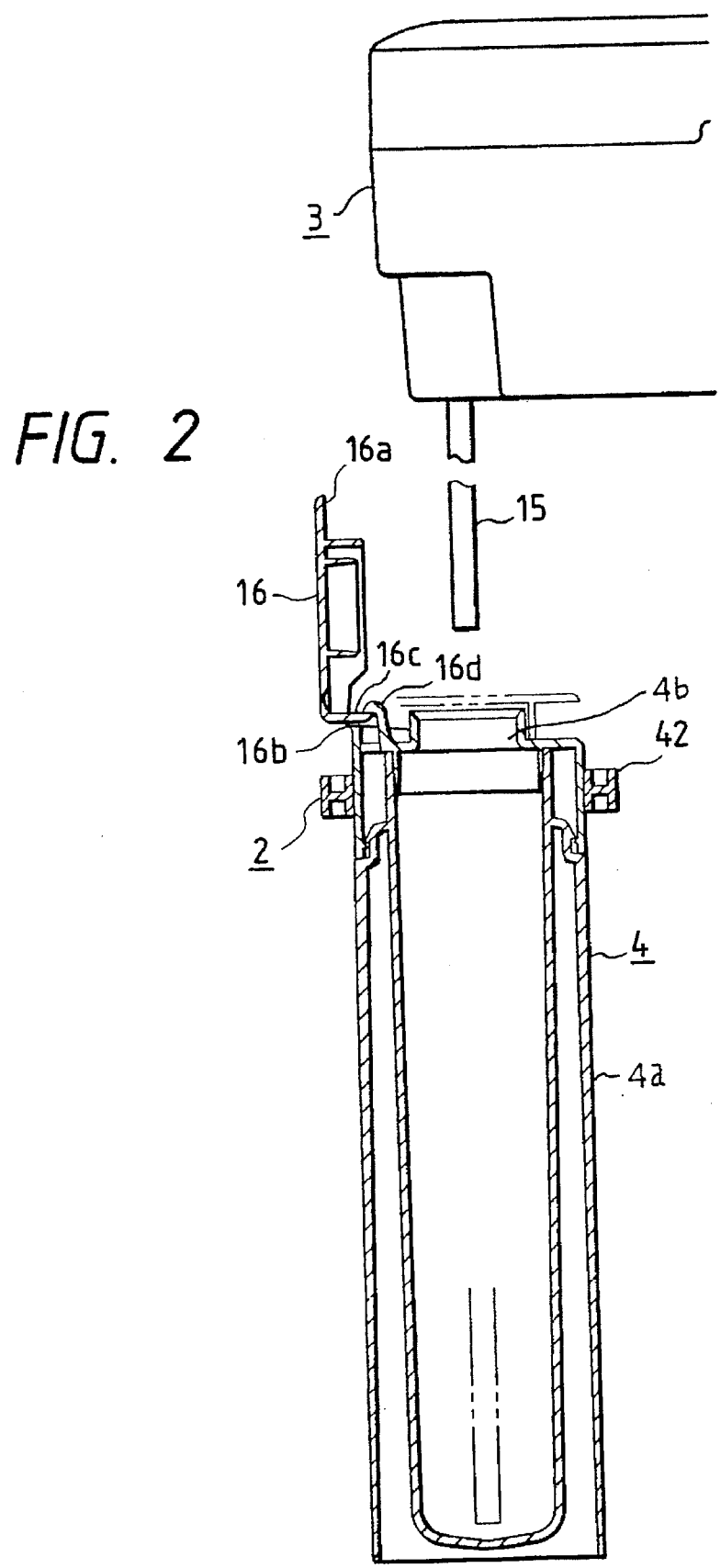
FIG. 2 is a view, partly in section, showing the positional relationship between a liquid container for a reagent and a nozzle of a pipetter installed in the analyzing apparatus of FIG. 1.

As shown in FIG. 2, each of the liquid containers 4 is provided with a container body 4a, an opening portion 4b and a lid, cover or cap 16 which has a projecting portion 16a at one end thereof, and which is coupled at the other end to the container body 4a with a hinge 16b so as to be rotated about the same. The container body 4a and the cap 16 are provided with projecting portions 16d and 16c, respectively. These projecting portions are engaged with each other when the cap 16 is rotated about the hinge 16b through an angle of 90° from a state where it completely closes the opening portion 4b, and its rotation is stopped when the projecting portions 16d and 16c are engaged with each other.

In FIG. 1, numeral 5 designates a sample container holding table which detachably holds a plurality of sample bottles, vessels or containers 43, and which is capable of not only transferring the sample containers 43 around the rotating shaft of a rotating mechanism by the rotating mechanism (not shown), but also positioning the sample containers at plural given positions. The pipetter 3 has a nozzle 15 (FIG. 2) for pipetting a reagent from the liquid container 4, whose opening portion is opened by manipulating the cap 16 by means of the cap manipulator device 1, and a moving mechanism (not shown) for moving the nozzle 15 in the horizontal and vertical directions. Numeral 6 designates a reaction vessel or container holder which holds disposable liquid receiving vessels or containers, i.e., reaction vessels or containers 44 used for reaction of a sample with the reagent, and which can control the temperature of the reaction container. A reaction container or vessel supplying storage, 7 always stores the reaction containers 44. A reaction measuring device 8 reacting state between a sample and a reagent. Numeral 9 designates a reaction container transfer mechanism for transferring the reaction container 44 from the reaction container supplying storage 7 to the reaction container holder 6, which has a moving mechanism (not shown) in the X-Y-Z direction. Numeral 10 designates a reacted liquid pipetting mechanism which sucks up the liquid inside the reaction vessel 44 on the reaction container holder 6 and delivers the sucked liquid to the reaction measuring device 8. A container collector 11 collects the used reaction containers 44. The analyzing apparatus also comprises a power source, a controller, an operating unit, a temperature controller, a display unit, a floppy disk driver, a printer, a pump and so on which are not shown in the figures.

Figure 3:
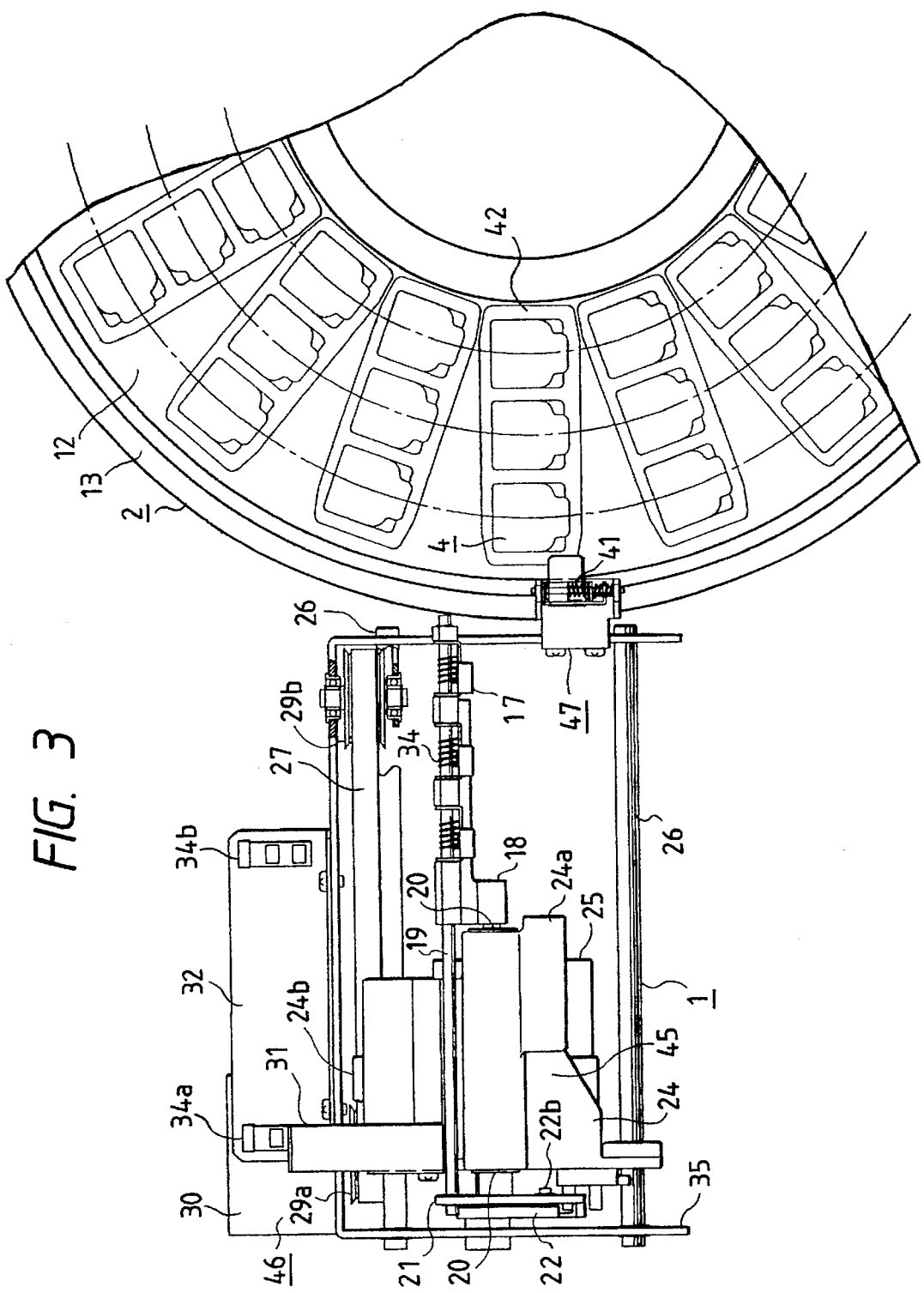
FIG. 3 is a top view showing the positional relationship between a movable container holding table, on which a plurality of liquid containers for reagents are arranged, and the cap manipulator device shown in FIG. 1.

As shown in FIG. 1 and FIG. 3, the reagent container storing device 2 has the rotatable reagent disk 12 for holding liquid container units, each of which is formed by integrating three reagent containers 4 in a row with a frame 42, a supporting shaft (not shown) for supporting the disk 12, a housing 13 for containing the liquid containers 4 together with the disk 12, and a cover 14 for covering the liquid containers 4 together with the disk 12. The cover is of an open structure so as not to prevent hooks 17 from entering. The disk 12 is rotated with a rotating mechanism to position the liquid containers 4 at plural given positions.

Figure 4:
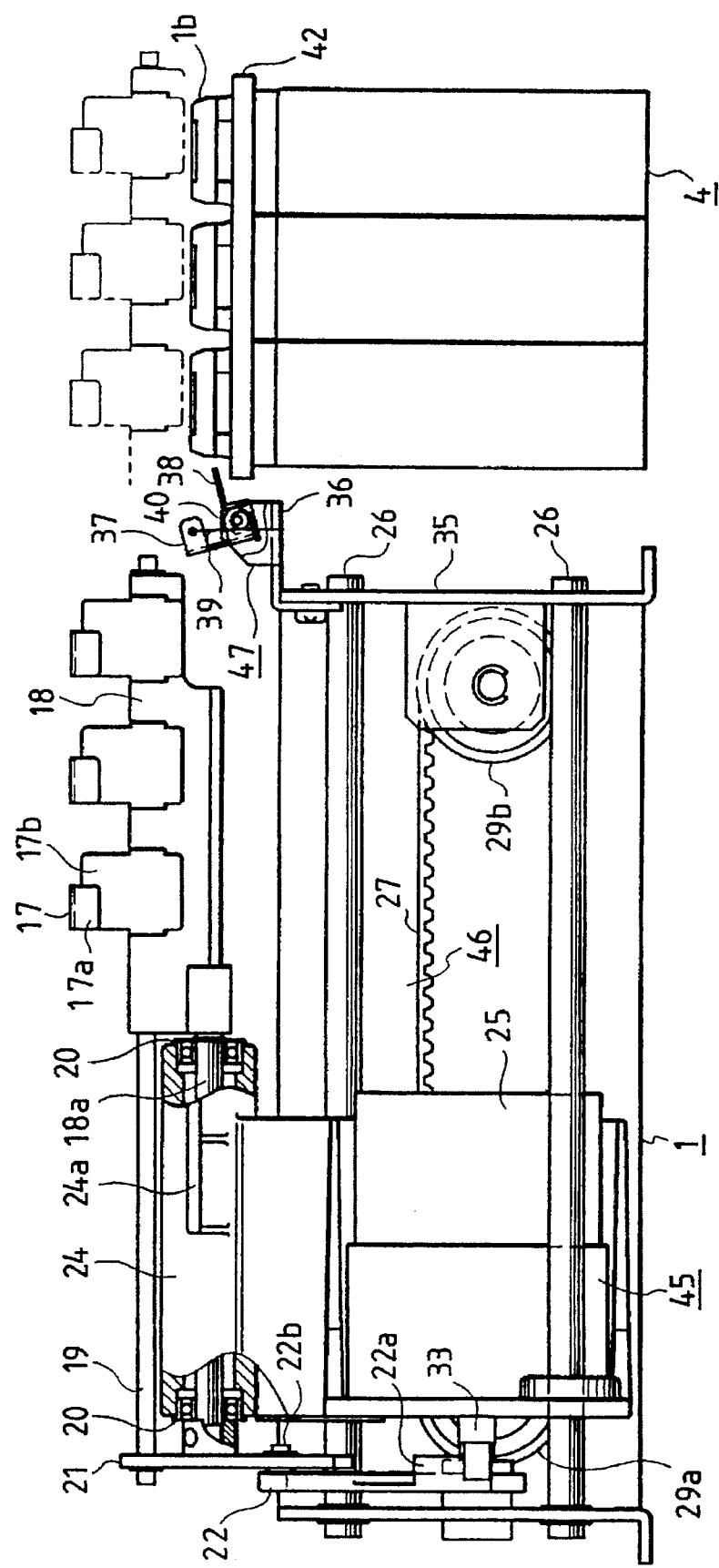
FIG. 4 is a side view of the movable container holding table, on which a plurality of liquid containers for reagents are arranged, and the cap manipulator device shown in FIG. 3.
Figure 5:
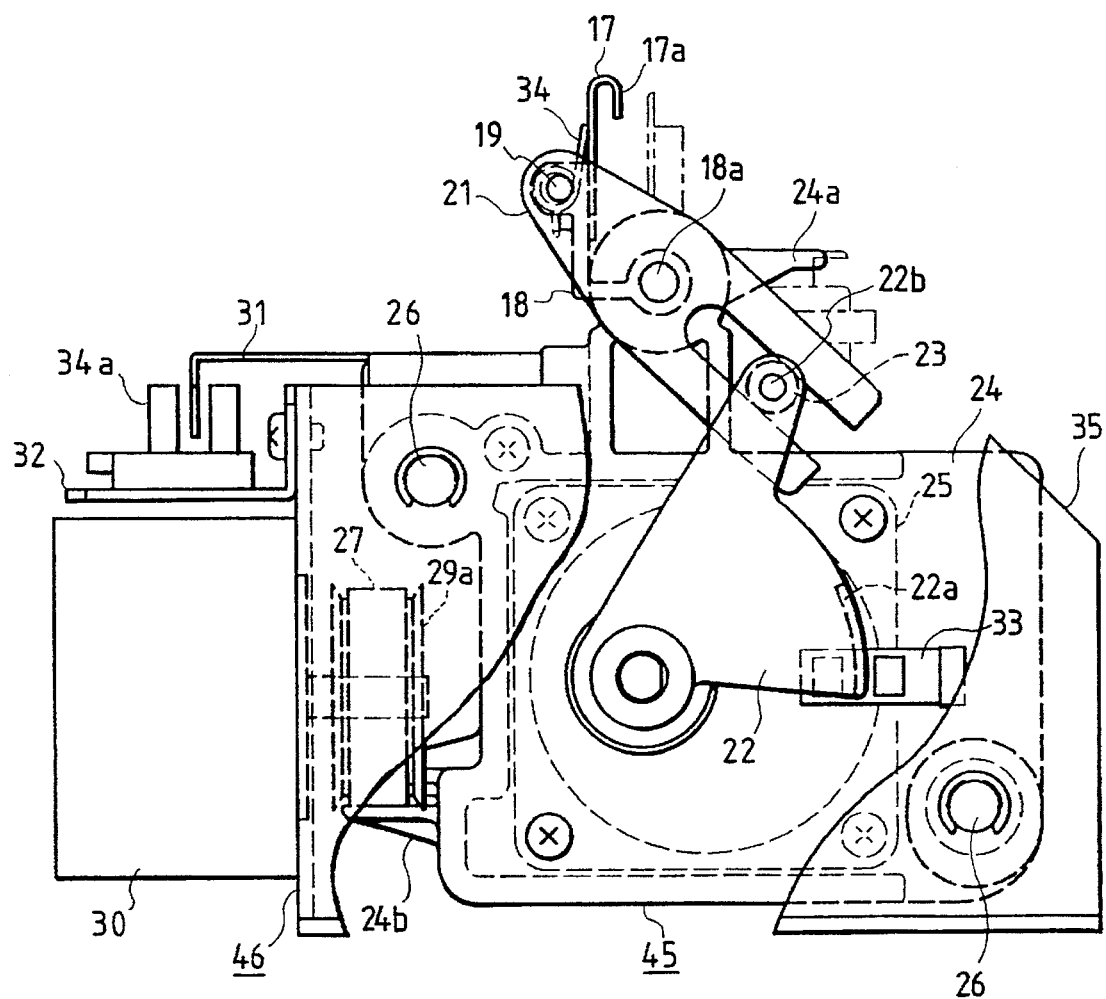
FIG. 5 is a front view of the cap manipulator device shown in FIG. 3.

The cap manipulator device 1 shown in FIG. 3 to FIG. 5 mainly comprises a cap manipulator 45 for manipulating the cap 16 so as to open and close the opening portion 4a, cap manipulator moving means 46 for horizontally moving the cap manipulator 45, and a container lift-up preventing device 47 for preventing the container body 4 from lifting up, that is, for keeping the same stationary.

The cap manipulator 45 comprises a hook 17 for manipulating the cap 16 by catching the projecting part 16a thereof and having a detection part 17b for detecting the topmost point of the cap 16 of the liquid container 4; a hook supporting shaft 19 for rotatably supporting the hook 17; a torsion coil spring 34 for pushing the hook 17 rotating around the supporting shaft 19 to the cap 16 of the liquid container; a hook supporting member 18 for supporting the hook 17, the torsion coil spring 34, and the hook supporting shaft 19, and having a rotating shaft 18; a ball bearing 20 for rotatably supporting the rotating shaft 18a of the hook supporting member 18; base 24 for supporting the hook supporting member 18 through the ball bearing 20; a driven link 21 fixed to the end portion of the rotating shaft 18a of the hook supporting member 18 and for giving rotating motion about the rotating shaft 18a of the hook supporting member 18; a main driving link 22 forming a crank mechanism with the driven link 21 and for driving the driven link 21; a roller bearing 23 placed between a pin 22b of the main driving link 22 and a slit of the driven link 21; a pulse motor 25 mounted on the base 24 for driving the main driving link 22; and a detector 33 for controlling the position for the opening and closing operation.

The cap manipulator moving means 46 of FIG. 5 comprises two horizontal supporting shafts 26 for supporting the base 24, a linear bearing (not shown) installed between the horizontal supporting shaft 26 and the base 24, a timing belt 27 connected to a belt fixing claw 24b of the base 24, a main driving pulley 29a for driving the timing belt 27, a driven pulley 29b, a pulse motor 30 for horizontal motion, a detected plate 31 for controlling the moving position in the horizontal direction, detectors 34a, 34b for detecting the horizontal position, a detector base 32 for mounting the detectors 34a, 34b, and a base 35. The cap manipulator moving means 46 is capable of moving the cap manipulator 45 in the horizontal direction. The container lift-up preventing device 47.

Show in FIG. 4 is a supporting shaft 40 for rotatably supporting a pushing plate 37 and a suppressing plate 38, a torsion coil spring 41 (FIG. 3) attached to the supporting shaft 40 and producing a suppressing force to suppress the lifting-up of the liquid container, a position adjusting torsion coil spring 39 attached to the supporting shaft 40 and adjusting position of the pushing plate 37, and a container lift-up preventing mechanism base 36 for supporting and mounting these parts on the base.

Operation of the apparatus will be described below by taking a typical process.

The initial positions of the cap manipulator 45 and its hook 17 of the cap manipulator device 1 are defined in order to explain the operation. As shown in FIG. 3 and FIG. 4, the initial position of the cap manipulator 45 is defined as a position where the hook 17 is in the farthest position from the three liquid containers integrated with the frame 42, and the initial position of the hook 17 is defined as its uppermost position. When the hook 17 is in the initial position, the detected part 22a of the main driving link 22 is in a position entering into the detector 33 by approximately 3.2 mm and the position of the driven link 21 is uniquely determined by the position of the main driving link 22. As a result, the position is determined as a position where the hook 17 is lifted up to its uppermost position.

The operation will be described below. Before starting analysis, the liquid containers 4 are set on the disk 12 of the reagent container storing device 2. During that time, the cap 16 is kept set so as to close the opening portion 4b of the liquid container 4, and there is no need to manipulate the cap in order to open the opening portion.

When the analysis is started after setting the liquid containers 4, the sample container holding table 5 and the reagent container storing device 2 rotate around the centers of the respective rotating mechanisms. The sample container holding table 5 transfers the sample container 43 containing a sample to be analyzed to a sample pipetting position which is an intersection of the horizontal moving locus 100 of the pipetter 3 and the rotational locus of the sample container 43. The reagent container storing device 2 transfers a plurality of liquid containers 4 containing the required reagents for individual analyzing items by rotational motion of the disk 12 to a manipulating position of the cap where the horizontal moving direction of the cap manipulator device 1 agrees with the direction of the rotational supporting shaft of the cap 16 and the position is in the side of the cap manipulator 1 on the reagent container storing device 2.

Then, the pipetter 3 horizontally moves the nozzle 15 to the sample pipetting position on the table 5 to suck or aspirate an amount of a sample required for the analysis from the sample container 43 and pours it into the reaction vessel 44.

Figure 6:
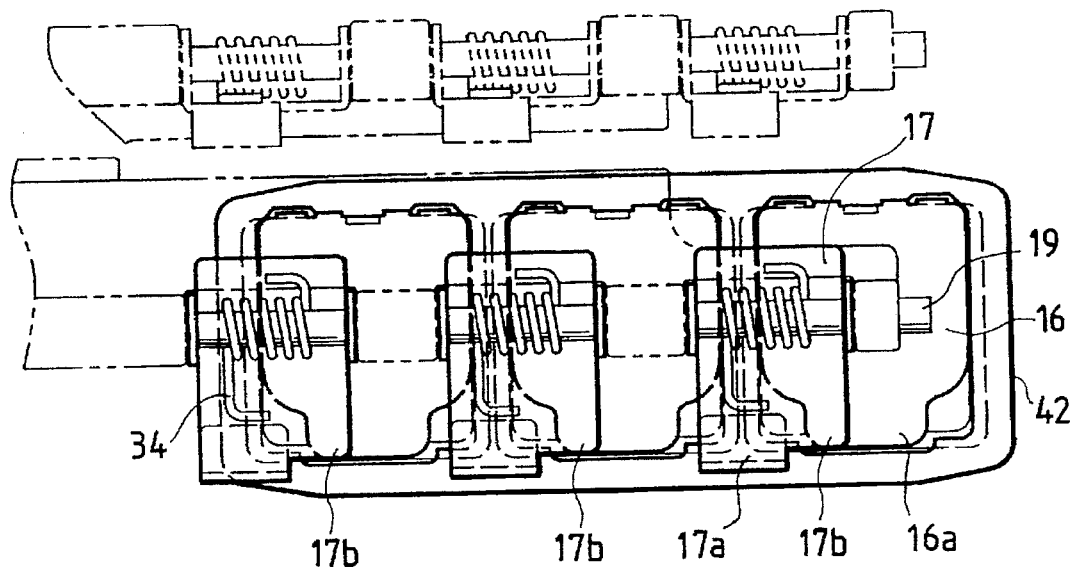
FIG. 6 is a top view showing the positional relationship between hooks provided in the cap manipulator device and corresponding caps of the liquid containers in a state where the hooks cannot be engaged with the corresponding caps.
Figure 8:
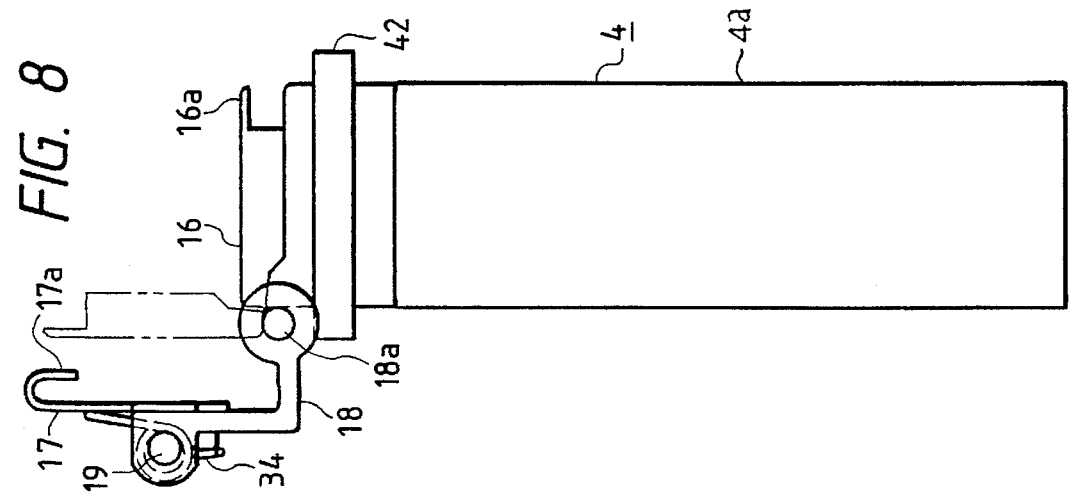
FIG. 8 is an explanatory view showing a state where the hook is at the initial position in a process of opening a opening portion of the liquid container by means of the cap manipulator device.

Next, the cap manipulator 45 of the cap manipulator device 1 moves toward and stops at the liquid container 4 placed in the cap manipulating position while the hook 17 is kept in the initial position shown in FIG. 8. The position of the hook 17 to the cap 16 when the cap manipulator stops is a position where the claw 17a of the hook 17 does not catch at the projecting part 16a of the cap 16 as shown in FIG. 6. The hook 17 shown in FIG. 8 comprises the detection part 17b and the claw 17a.

Figure 10:
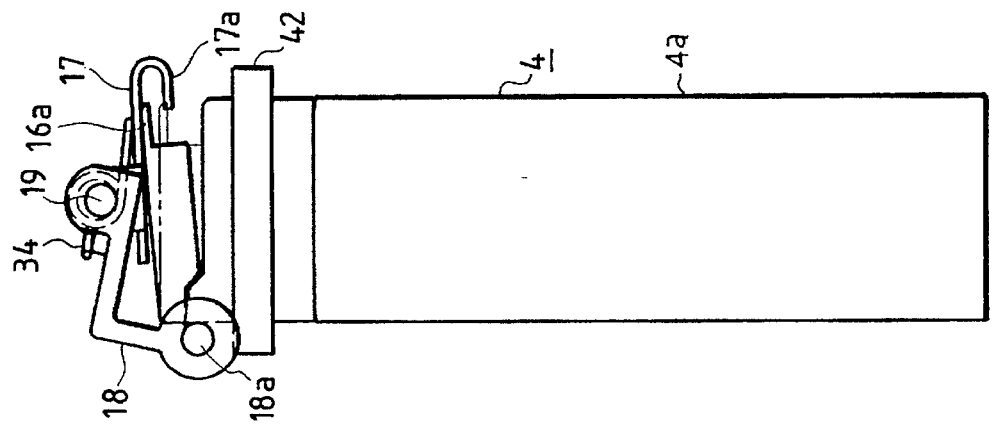
FIG. 10 is an explanatory view showing a state where the hook is lowered to the cap of the liquid container, in a state where the cap is set so as to slightly open the opening portion of the liquid container, in a process of opening the same by means of the cap manipulator device.
Figure 9:
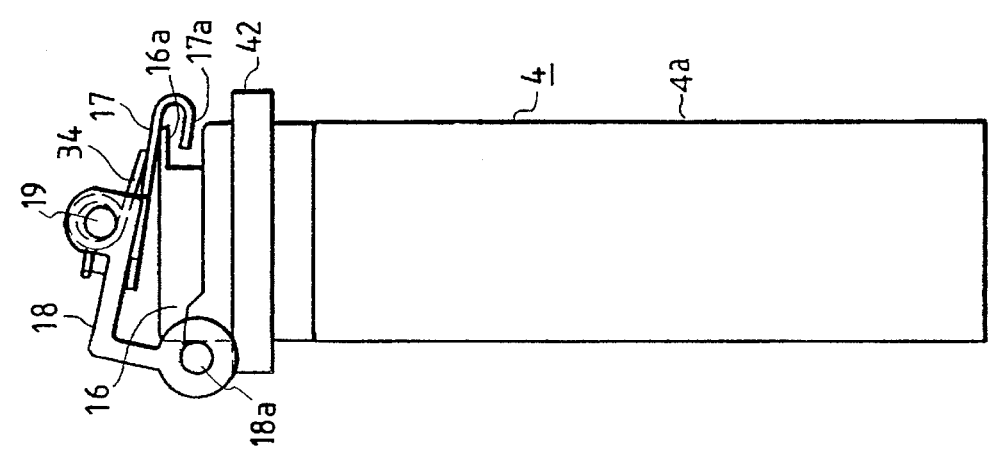
FIG. 9 is an explanatory view showing a state where the hook is lowered to the cap of the liquid container, in a state where the cap is set so as to completely close the opening portion of the liquid container, in a process of opening the same by means of the cap manipulator device.

As to the hook shown in FIG. 6, the hook 17 drawn by a two dotted chain line shows the hook 17 in the initial position, and the hook 17 drawn by solid line shows the hook 17 in a state where the hook is lowered to the lowermost position to the cap set so as to completely close the opening portion of the liquid container as shown in FIG. 9, or shows the hook 17 in a state where the hook is lowered to the lowermost position to the cap set so as to slightly open the opening portion of the liquid container as shown in FIG. 10 in the manipulating process of the cap for opening the opening portion of the liquid container shown in FIG. 8 to FIG. 11. The direction moving the hook 17 from the initial position of the cap manipulator 45 to the position shown in FIG. 6 is defined as a forward direction; moving, in the forward direction is called "forward moving" and moving in the opposite direction is called "backward moving".

The forward moving of the hook 17 to the position of FIG. 6 is performed in such a way that clockwise rotation of the pulse motor 30 for horizontal movement rotates the main driving pulley 29a and the timing belt 27, and the base 24 joined to the timing belt 27 with the belt fixing claw 24b is, therefore, driven. The stopping position is controlled by detecting the detection plate 31 fixed to the base 24 with the detector 34b.

After the hook 17 is stopped, it is driven by the pulse motor 25 to be lowered near the rotating shaft 18a of the hook supporting member 18, and it reaches a state shown by FIG. 9 or FIG. 10.

This operation is performed with a crank mechanism of the cap manipulator 45 to be described below. By counterclockwise rotation of the pulse motor 25, the main driving link 22 fixed to the pulse motor 25 with screws is also rotated counterclockwise. The force by rotation of the main driving link 22 is transmitted to the driven link 21 while the roller bearing 23 is placed in the pin 22b of the main driving link 22, and the driving link 21 is rotated clockwise around the rotating shaft 18a of the hook supporting member 18. At that time, the roller bearing 23 serves to decrease the loss of force and the abrasion due to the friction between the main driving link 22 and the driven link 21. Since the driven link 21 is fixed to the end of the rotating shaft 18a of the hook supporting member 18 with screws, the rotating force of the driven link 21 is transmitted to the hook supporting member 18 to rotate the hook supporting member 18 together with the driven link 21. Therefore, the hook 17 also rotates clockwise since the hook 17 is supported with the hook supporting member 18.

The above is the operation of the crank mechanism in the cap manipulator 45 and the operation of the hook 17 accompanied by the operation of the crank mechanism.

When the hook is lowered, the amount of movement in rotation of the hook supporting member 18 is controlled by the number of pulses given to the pulse motor 25. The hook supporting member 18 is lowered to and stopped at a position when the detection part 17b of the hook 17 touches the uppermost point of the cap 16 as shown in FIG. 9 or FIG. 10 and the torsion coil spring 34 is bent. At that time, the position of the hook 17 is automatically adjusted by the torsion coil spring 34 in such a way as to meet with the cap 16 by touching of the detection part 17b to the topmost point of the cap 16 in the liquid container 4 as shown in FIG. 9 or FIG. 10 depending on the state of the bottle cap 16, and then stopped. FIG. 9 shows a state where the cap 16 is set so as to completely close the opening portion, and FIG. 10 shows a state where the cap 16 is set so as to slightly open the opening portion. The difference in level of the cap caused by the individual difference due to variation in the dimension of the liquid container and the difference in the opening degree of the opening portion can be absorbed by the torsion coil spring 34, by which the position of the hook 17 is automatically adjusted. Further, it is also possible to absorb the relative difference among the liquid containers due to the deviation in the dimension of the liquid container, the manufacturing allowance and dimensional allowance of the apparatus caused in a case where a plurality of opening portions are opened at a time.

Figure 7:
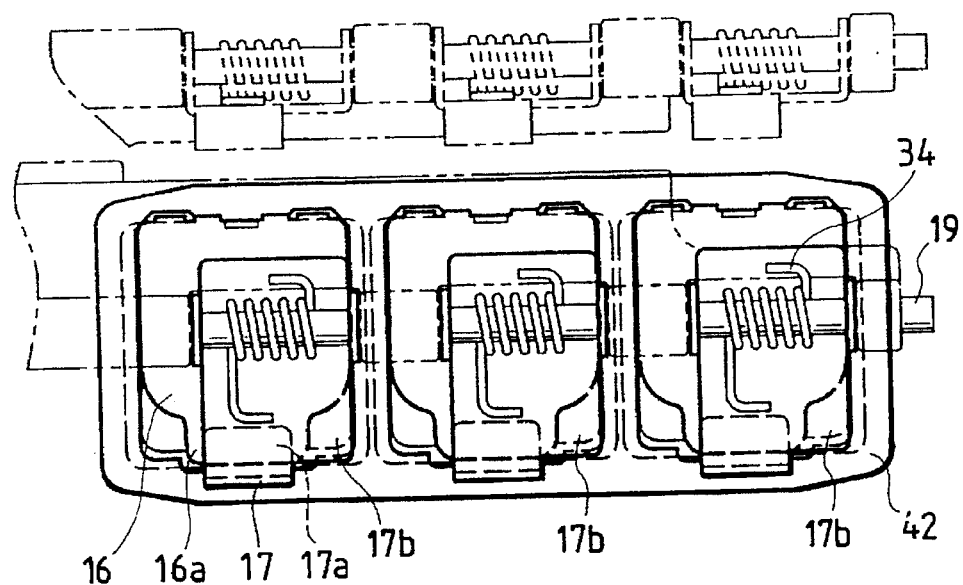
FIG. 7 is a top view showing the positional relationship between hooks provided in the cap manipulator device and corresponding caps of the liquid containers in a state where the hooks can be engaged with the corresponding caps.

When the hook 17 is stopped in the state shown in FIG. 9 or FIG. 10, the cap manipulator 45 starts the forward moving while keeping the state, and proceeds up to a position where the claw 17a of the hook 17 shown in FIG. 7 overlaps with the projecting part 16a of the cap 16 and stops. The amount of movement is controlled by the number of pulses given to the pulse motor 30 for moving.

Figure 11:
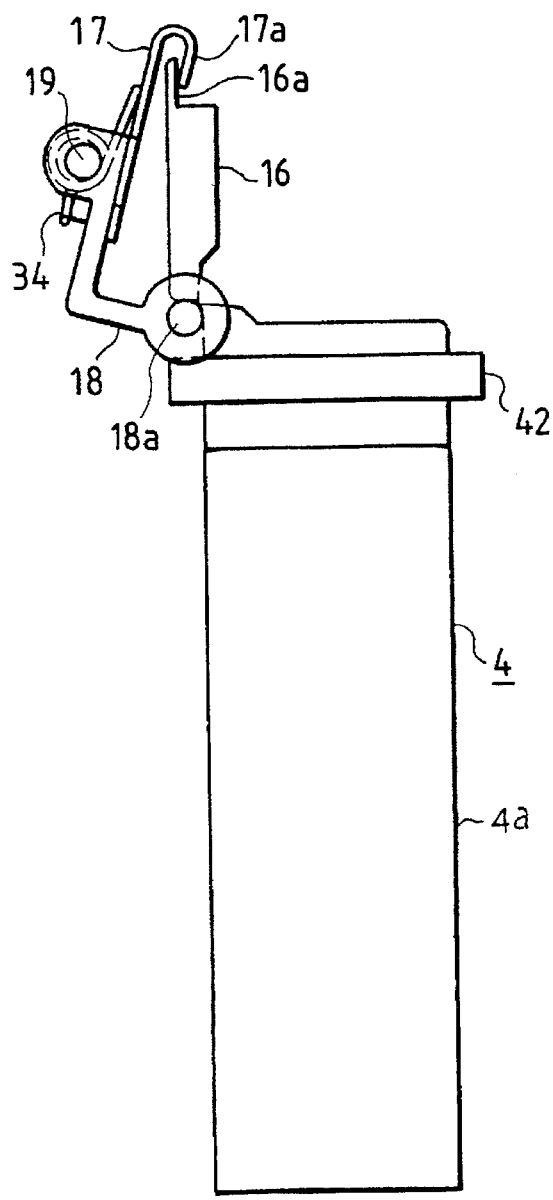
FIG. 11 is an explanatory view showing a state where the cap of the liquid container is at an angular position of 90° with the hook being engaged with the cap.

Then, the hook 17 is lifted up about the rotating shaft 18a of the hook supporting member 18 by the crank mechanism of the cap manipulator 45, and stops at the position shown in FIG. 11. At that time, the claw 17a of the hook 17 catches the projecting part 16a of the cap of the liquid container 4 and manipulates the cap so as to open the opening portion by generating a rotating force agreeing with the opening direction of the opening portion. This operation is performed in such a way that the main driving link 22 is rotated clockwise by the clockwise rotation of the pulse motor 25, and accordingly the hook supporting member 18 is rotated counterclockwise about its rotating shaft 18a together with the driven link 21. The stopped position of the hook 17 shown in FIG. 11 is a position where the cap 16 is rotated by an angle of 90° in order to completely open the opening portion. The stopped position is controlled by the number of pulses given to the pulse motor 25. If the liquid container 4 is not fixed to the disk 12, the liquid container 4 is lifted up by the force of the hook 17 for manipulating the cap 16 when the opening portion is opened. Therefore, in order to prevent the liquid container 4 from lifting-up, it is necessary to fix the liquid container 4 to the disk 12 with some means.

In the apparatus of the embodiment, the container lift-up preventing device 47 is used to suppress the lifting-up of the liquid container 4. The lift-up preventing device 47 serves as follows.

When the motor 30 moves the base 24 forward to transfer the hook 17 to the position shown in FIG. 7, a fin 24a of the base 24 proceeds forward while pushing the pushing plate 37. The pushing plate 37 pushed by the fin 24a is rotated about the supporting shaft 40, and interposed between the pushing plate 37 and the suppressing plate 38 to rotate the suppressing plate 38 about the supporting shaft 40 at the same time by the torsion coil spring 41 attached to the supporting shaft 40. Although the suppressing plate 38 stops rotating the suppressed plate touches the frame 42, the pushing plate 37 continues to rotate to some extent after the suppressing plate stops until the base 24 stops. That is, the gap between the pushing plate 37 and the suppressing plate 38 is decreased and the torsion coil spring 41 interposed between the two plates is bent. The recovering force of the bent torsion coil spring 41 becomes a suppressing force to suppress lifting-up of the liquid container 4 to prevent the same from lifting-up.

As described above, the lift-up preventing device 47 is operated by forward movement of the base 24 to suppress lifting-up of the liquid container 4 when the cap is lifted with the hook 17.

After the hook 17 lifts up the cap 16 around about its rotating supporting point, the cap manipulator 45 is moved backward while keeping its state as it is, and the hook 17 is returned to the position shown in FIG. 6. By returning the hook 17 to the position shown in FIG. 6, the claw 17a of the hook 17 is detached from the projecting part 16a of the cap 16. The cap 16 can be kept stationary at an angle of 90° with respect to the horizontal even when the claw 17a of the hook 17 is detached.

As the base 24 moves backward, the pushing plate 37 is released from the pushing force of the fin 24a. When the pushing plate 37 is released from the pushing force of the fin 24a, the position of the pushing plate 37 is returned to the original position by the coil spring 39 for adjusting position. At the same time, the suppressing plate 38 is also returned to the original position and the force to suppress the bottle is eliminated.

After backward moving of the cap manipulator 45, the hook 17 is raised up to the initial position shown in FIG. 8 by the crank mechanism. The stopping of the hook 17 at the initial position is controlled by detection of the detection part 22a of the main driving link 22 with the detector 33.

The cap manipulator 45 is driven by the pulse motor 30 for horizontally moving while the hook 17 is kept in the initial position and returned to the initial position which is positioned set by detection of the detection plate 31 with the detector 34a, and the opening operation is completed. The cap manipulator device 1 placed in the initial position after completion of opening operation does not interfere with operations of the other mechanisms of the apparatus at all.

The above is the procedure of opening the opening portion of the liquid container 4 using the cap manipulator device 1. Although three caps are simultaneously manipulated in this embodiment, only one cap or two bottle caps may be simultaneously manipulated. It is also possible to simultaneously manipulate four or more caps for simultaneously opening four or more opening portions by increasing the number of the hooks 17 and the number of the liquid containers arranged on the disk 12.

Next, among the three liquid containers 4 whose opening portions are opened, a liquid container containing a reagent required for analysis is transferred to the pipetting position by rotation of the disk 12 to be pipetted. The pipetting positions of the liquid containers 4 coincide with the intersections of the locus of the nozzle position due to the horizontal movement of the pipetter 3 and the moving locus of the entrance of the liquid containers due to rotation of the disk 12. It is, therefore, possible to pipette from a liquid container 4 placed at the inner side of the disk 12, and it is also possible to improve the efficiency of pipetting from an arbitrary liquid container 4. As a result it is possible to shorten the time during which the opening portion of the liquid container 4 is kept open.

After sucking of the required reagent, the pipetter 3 moves the nozzle 15 onto the reaction container 44 to deliver the reagent. After repeating of pipetting of reagent from the other reagent bottles 4 in a similar way, the pipetting operation is completed.

As shown in FIG. 1, since the pipetter 3 of the embodiment is installed so that the horizontal moving locus of the nozzle of the pipetter and the rotating locus of liquid containers 4 arranged in the reagent bottle holding mechanism 2 have intersections, and the horizontal moving locus of the nozzle of the pipetter and the rotating locus of the sample containers 43 arranged in the sample bottle holding mechanism 5 have an intersection, both pipetting of sample and pipetting of reagent can be performed using the same pipetter 3.

After a certain time has elapsed, the liquid in the reaction container 44 is pipetted to the reaction measuring mechanism 8 using the reacted liquid pipetting mechanism 10. The reaction container 44 after completion of pipetting is transferred to the disposing container 11 with the reaction container transfer mechanism 9, to be disposed.

Then, the reaction container transfer mechanism 9 transfers a new reaction container 44 from the reaction container storage 7 to the reaction container holding mechanism 6 in order to prepare the next analysis.

The operation of the reacted liquid pipetting mechanism 10, the reaction measuring mechanism 8 and the reaction container transfer mechanism 9 can be composed using well known technologies and mechanisms.

On the other hand, after completion of the pipetting of reagent, the liquid container 4 whose opening portion is opened is transferred to the cap manipulating position by rotation of the disk 12.

When the disk 12 is stopped, the cap manipulator 45 of the cap manipulator device 1 is moved forward by the horizontal moving mechanism, and the hook 17 is moved up to the position shown in FIG. 7. The amount of the movement is controlled by the number of pulses given to the pulse motor 30.

Figure 12:
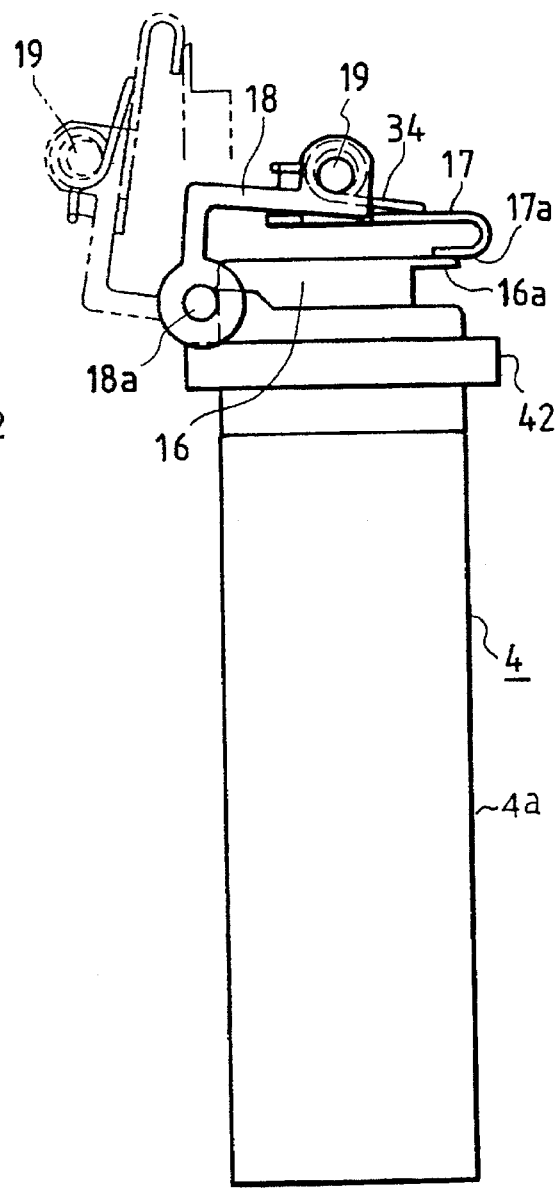
FIG. 12 is an explanatory view showing a state where the opening portion of the liquid container is closed by rotating the hook with the same being engaged with the cap, in a process of closing the opening portion of the liquid container by means of the cap manipulator device.

Then, as shown in FIG. 12, the hook 17 moves downward and manipulates the cap 16 so as to close the opening portion of the liquid container while the claw 17a of the hook 17 gives a rotating force to the top surface of the cap 16 by rotating the hook about the rotating shaft 18a of the hook supporting member 18. At that time, the rotation of the hook supporting member 18 is controlled by the number of pulses given to the pulse motor 25. When the cap 16 is manipulated so as to close the opening portion of the liquid container, the individual difference due to deviation in dimension of the liquid containers 4 and the relative difference among the liquid containers 4 when a plurality of liquid containers are operated at a time become a problem. However, the problem can be solved by the automatic adjusting function of the torsion coil spring 34 similarly to the problem in the opening operation. Further, by employing torsion coil springs having different recovering forces, the closing degree of the opening portion with the cap 16 can be adjusted. After the opening portion is closed, the hook 17 is returned to the initial position shown in FIG. 8 by the operation of the crank mechanism.

After that, the cap manipulator 45 is returned to the initial position, and the closing operation is completed. Although three opening portions are simultaneously closed in this embodiment, two or fewer opening portions may be simultaneously closed. It is also possible to simultaneously close four or more opening portions by modifying the construction a little.

Analysis is continued by repeating the above operation.

In the cap manipulator device 1 according to the present invention, the cap manipulator 45 is constructed with a crank mechanism. However, the mechanism may be constructed with gears or a timing belt. Similarly, although the horizontal moving using the cap manipulator moving means 46 is performed with a timing belt, a rack-and-pinion mechanism or the like may be employed. Further, although the cap manipulator device 1 in the embodiment manipulates the cap 16, the liquid container is not limited to that for reagents, and the opening and closing operation of a liquid container is possible so long as the bottle and the cap are integrated in a unit.

Furthermore, the movement of the pipetter 3 is not limited to straight moving. The pipetter may be rotated, for example, around the supporting shaft which supports the pipetter so long as the pipetter 3 comprises a horizontally moving means such as to form intersections with the rotating locus of the plural liquid containers arranged in the container holding mechanism.

Since the embodiment of the analyzing apparatus described above can handle the liquid container in which the container body and the cap are integrated in a unit, an operator is released from the complex work of attaching and detaching the liquid containers, which is required when the liquid containers are set or stored in the apparatus.

The cap manipulator device drives the hook, so that the force required for manipulating the cap becomes a rotating force, the direction of which agrees with the direction of opening and closing the opening portion. Therefore, the cap manipulator can suppress loss in the force to open and close the opening portion to the minimum, and can certainly perform opening and closing of the opening portion with a small force. Further, evaporation of the content in the liquid container can be effectively prevented.

The cap manipulator device has a mechanism which horizontally moves in the direction of a row of the liquid containers arranged in a line, can access the liquid containers only when the opening portions of the liquid containers are to be opened or closed, and can be drawn back without interrupting the operations of the other mechanisms of the analyzing apparatus when opening or closing of the opening portions of the liquid containers is not required. Therefore, there is no need to stop the operations of the other mechanisms during analysis, and accordingly there is an effect to shorten the operating time of the analyzing apparatus.

Since the cap manipulator device has the cap manipulator and the cap manipulator moving means, both operations of manipulating the cap to open and close the opening portions of the liquid containers can be performed with the same mechanism. Since the cap manipulator has a mechanism for adjusting the position of the hook so as to meet with the position of the cap, the individual difference due to deviation in the dimension of liquid containers, the manufacturing allowance and the dimensional allowance of the apparatus, and the relative differences among individual liquid containers appearing when a plurality of liquid containers are used, can be absorbed, and consequently a plurality of caps can be manipulated simultaneously.

The container storing device is capable of transmitting the liquid containers around the center of the disk for supporting the liquid containers, and is capable of positioning the liquid containers at plural given positions. The pipetter has the horizontal moving means and the vertical moving means serving above the container storing device. Therefore, pipetting of the contents in the liquid containers can be performed at plural intersecting points determined by the moving locus of the pipetter in the horizontal direction and by the rotating locus of the plural liquid containers arranged in the radial direction of the container storing device, and the efficiency of pipetting can be improved. Consequently, since evaporation can be prevented by shortening the opening time of the opening portion of the liquid container, it is possible to provide an analyzing apparatus capable of performing an accurate analysis for a long time without calibration.

According to the present invention, since a liquid container comprises a container body, an opening portion and a cap coupled to the container body, and since the cap is manipulated by a cap manipulator device so that the opening portion is opened and closed, the opening and closing operation can be certainly performed automatically. The setting position of the bottle in a transfer device can be freely changed, and the limitation to limit the number of reagent kinds is eliminated. Further, in the present invention, existence of the cap manipulation device does not interfere with maintenance work or inspection work of the container transfer device in the container storing device. Furthermore, by providing a plurality of hooks, it is possible to simultaneously open and close the opening portions of a plurality of liquid containers required in the same analyzing item.

What is claimed is:

1. An apparatus for transferring a liquid from a liquid container to a liquid receiving container, comprising:
   a movable container holding table for holding a plurality of liquid containers, each of the liquid containers having a container body accommodating a liquid, an opening portion, and a cap attached to the container body so as to be capable of opening and closing the opening portion;
   a cap manipulator for manipulating the cap so as to open the opening portion;
   a pipetter for aspirating the liquid in the liquid container whose opening portion is opened therethrough and delivering the aspirated liquid to a liquid receiving container; and
   means for moving the cap manipulator between first and second positions spaced apart from each other, the cap manipulator manipulating the cap so as to open the opening portion at the first position;
   wherein the cap is hinged to the liquid container body so as to be rotatable around a fist rotating axis;
   wherein each cap has a projecting portion and the cap manipulator comprises a hook, the cap manipulator engaging the hook with the projecting portion and moving the hook so as to open the opening portion of the liquid container having the protecting portion with which the hook is engaged;
   wherein the hook has a second rotating axis positioned in the proximity of the first rotating axis so as to be rotated around the second rotating axis; and
   wherein the cap manipulator rotates the hook around the second rotating axis in a first rotating direction so that the hook is directed to the cap, moves the hook in a horizontal direction so that the hook is located at a position at which the hook is capable of being engaged with the projecting portion and then rotates the hook around the second rotating axis in a second rotating direction reverse to the first rotating direction with the hook being engaged with the projecting portion so as to open the opening portion.

2. An apparatus according to claim 1, wherein the cap manipulator comprises a contact portion integrated with the hook, the contact portion contacting the cap when the hook is rotated in the first rotating direction, and means for elastically urging the contact portion in the first rotating direction.

3. An apparatus according to claim 2, wherein the contact portion urging means comprises a coil spring.

4. An apparatus according to claim 1, wherein the cap manipulator rotates the hook in the first rotating direction so as to bring the hook into contact with the cap to close the opening portion of the liquid container having the cap into contact with which the hook is brought.

5. An apparatus according to claim 2, wherein the cap manipulator rotates the hook in the first rotating direction so as to bring the hook into contact with the cap to close the opening portion of the liquid container having the cap into contact with which the hook is brought.

6. An apparatus according to claim 3, wherein the cap manipulator rotates the hook in the first rotating direction so as to bring the hook into contact with the cap to close the opening portion of the liquid container having the cap into contact with which the hook is brought.

7. An apparatus for transferring a liquid from a liquid container to a liquid receiving container, comprising:
   a movable container holding table holding a plurality of liquid containers, each of the liquid containers having a container body accommodating a liquid, an opening portion, and a cap having a projection portion, the cap being attached to the container body so as to be capable of opening and closing the opening portion;
   a cap manipulator for manipulating the cap to open the opening portion, the cap manipulator having a hook;
   a cap manipulator moving device for moving the cap manipulator in first and second mutually opposite directions, the cap manipulator approaching the cap when moved in the first direction; and
   a pipetter for aspirating the liquid in the liquid container whose opening portion is opened, and for delivering the aspirated liquid to a liquid receiving container;
   wherein the cap manipulator rotates the hook about a predetermined rotating axis in a first rotating direction so that the hook is directed to the cap, moves the hook in a third direction transverse to the first and second directions, whereby the hook is located at an engagement position with respect to the projecting portion, and then rotates the hook about the predetermined rotating axis in a second rotating direction opposite to the first rotating direction, with the hook being engaged with the projecting portion to open the opening portion.

8. An apparatus according to claim 7, wherein the cap is rotatably hinged to the liquid container body.

9. An apparatus according to claim 8, wherein the cap manipulator comprises a contact portion integrated with the hook, the contact portion contacting the cap when the hook is rotated in the first rotating direction, and a coil spring elastically urging the contact portion in the first rotating direction.

10. An apparatus according to claim 9, wherein the cap manipulator rotates the hook in the first rotating direction so as to bring the hook into contact with the cap to close the opening portion of the liquid container having the cap into contact with which the hook is brought.

11. An apparatus according to claim 10, further comprising means for keeping the container body of the liquid container stationary when the opening portion thereof is opened.

12. An apparatus according to claim 11, wherein the liquid is a reagent.

13. An apparatus for transferring a liquid from a liquid container to a liquid receiving container, comprising:

a movable container holding table holding a plurality of liquid containers, each of the liquid containers having a container body accommodating a liquid, an opening portion, and a cap having a projection portion, the cap being attached to the container body so as to be capable of opening and closing the opening portion;

a cap manipulator for manipulating the cap to open the opening portion, a cap manipulator moving device for moving the cap manipulator in first and second mutually opposite directions, the cap manipulator approaching the cap when moved in the first direction; and a pipetter for aspirating the liquid in the liquid container whose opening portion is opened, and for delivering the aspirated liquid to a liquid receiving container;

wherein the cap manipulator has a plurality of hooks, and the cap manipulator integrally rotates the plurality of hooks about a predetermined rotating axis in a first rotating direction so that the plurality of hooks are directed to corresponding ones of the plurality of caps; integrally moves the plurality of hooks in a third direction transverse to the first and second directions, whereby the plurality of hooks are located at engagement positions with corresponding projecting portions; and then integrally rotates the plurality of hooks about the predetermined rotating axis in a second rotating direction opposite to the first rotating direction with the plurality of hooks being engaged with the corresponding projecting portions to open corresponding opening portions the liquid containers.

14. An apparatus according to claim 13, wherein the cap manipulator integrally rotates the plurality of hooks in the first rotating direction so as to bring the plurality of hooks into contact with the corresponding caps to substantially simultaneously close the opening portions of the liquid containers having the caps with which the plurality of hooks are brought into contact.

15. An apparatus according to claim 14, wherein the cap manipulator comprises contact portions respectively integrated with the plurality of hooks, the contact portions contacting the corresponding caps when the plurality of hooks are integrally rotated in the first rotating direction; and coil springs elastically urging the contact portions in the first rotating direction.

16. An apparatus for handling a liquid in a liquid container comprising:

a movable container holding table holding a plurality of liquid containers, each of the liquid containers having a container body accommodating a liquid, an opening portion, and a cap having a projection portion, the cap being attached to the container body so as to be capable of opening and closing the opening portion;

a cap manipulator for manipulating the cap to open the opening portion, the cap manipulator having a hook; and a cap manipulator moving device for moving the cap manipulator in first and second mutually opposite directions, the cap manipulator approaching the cap when moved in the first direction;

wherein the cap manipulator rotates the hook about a predetermined rotating axis in a first rotating direction so that the hook is directed to the cap, moves the hook in a third direction transverse to the first and second directions, whereby the hook is located at an engagement position with respect to the projecting portion, and then rotates the hook about the predetermined rotating axis in a second rotating direction opposite to the first rotating direction, with the hook being engaged with the projecting portion to open the opening portion.

17. An apparatus according to claim 16, wherein the cap is rotatably hinged to the liquid container body.

18. An apparatus according to claim 17, wherein the cap manipulator comprises a contact portion integrated with the hook, the contact portion contacting the cap when the hook is rotated in the first rotating direction, and a coil spring elastically urging the contact portion in the first rotating direction.

19. An apparatus according to claim 18, wherein the cap manipulator rotates the hook in the first rotating direction so as to bring the hook into contact with the cap to close the opening portion of the liquid container having the cap with which the hook is brought into contact.

20. An apparatus according to claim 19, further comprising means for keeping the container body of the liquid container stationary when the opening portion thereof is opened.

21. An apparatus according to claim 20, wherein the liquid is a reagent.

* * * * *